(12) United States Patent
Zou et al.

(10) Patent No.: US 10,876,962 B2
(45) Date of Patent: Dec. 29, 2020

(54) METHOD AND DEVICE FOR ON-LINE DETECTION OF SALINITY OF SEATER

(71) Applicant: SHENZHEN POLYTECHNIC, Guangdong (CN)

(72) Inventors: Bo Zou, Guangdong (CN); Yang Wang, Guangdong (CN)

(73) Assignee: Shenzhen Polytechnic, Guangdong (CN)

( * ) Notice: Subject to any disclaimer, the term of this patent is extended or adjusted under 35 U.S.C. 154(b) by 453 days.

(21) Appl. No.: 15/778,631

(22) PCT Filed: Jun. 2, 2017

(86) PCT No.: PCT/CN2017/087086
§ 371 (c)(1),
(2) Date: May 24, 2018

(87) PCT Pub. No.: WO2017/206956
PCT Pub. Date: Dec. 7, 2017

(65) Prior Publication Data
US 2018/0356340 A1   Dec. 13, 2018

(51) Int. Cl.
*G01N 21/45* (2006.01)
*G01N 21/41* (2006.01)
(Continued)

(52) U.S. Cl.
CPC ......... *G01N 21/45* (2013.01); *G01K 11/3206* (2013.01); *G01N 21/4133* (2013.01);
(Continued)

(58) Field of Classification Search
None
See application file for complete search history.

(56) References Cited

U.S. PATENT DOCUMENTS

| 6,043,922 A * | 3/2000 | Koga ............... H04B 10/69 398/213 |
| 2005/0109080 A1* | 5/2005 | Hok ............... G01N 29/036 73/24.01 |

(Continued)

FOREIGN PATENT DOCUMENTS

| CN | 1374529 | 10/2002 | |
| CN | 10875987 | * 6/2006 | ............... G01D 5/30 |

(Continued)

OTHER PUBLICATIONS

Xiaohong Quan and Edward S. Fry, "Empirical equation for the index of refraction of seawater", Applied Optics, Jun. 20, 1995, pp. 3477-3480.

(Continued)

*Primary Examiner* — Tung S Lau
(74) *Attorney, Agent, or Firm* — JCIPRNET

(57) ABSTRACT

The present invention provides a method and device for on-line detection of the salinity of seawater. A sweep frequency synchronous signal controls a sweep frequency laser light source such that the wavelength of a frequency modulation light wave output by the sweep frequency laser light source is a periodic saw-tooth wave signal. The frequency modulation light wave is divided into two beams, respectively transmitted to a refractive index probe and a temperature probe in seawater. The refractive index probe is an interference instrument structure, and the frequency value of an interference light intensity signal fed back by the refractive index probe is related to the refractive index of seawater. The refractive index of seawater is calculated by performing discrete Fourier transformation on the interference light intensity signal. The temperature probe is internally provided with a fiber Bragg grating, and the Bragg wavelength of the reflection spectrum of the temperature probe is related to the temperature of the seawater. The sweep frequency (Continued)

synchronous signal and the reflection light intensity signal of the fiber Bragg grating are subjected to synchronous discrete sampling, and the temperature value of the seawater is calculated according to a grating temperature sensor demodulation algorithm. The salinity value of the detected seawater is obtained by solving an empirical equation according to the obtained refractive index, the temperature value and the average wavelength of the frequency modulation light wave, thereby implementing on-line detection of the salinity of seawater.

16 Claims, 1 Drawing Sheet

(51) Int. Cl.
  *G01N 21/85* (2006.01)
  *G01N 33/18* (2006.01)
(52) U.S. Cl.
  CPC ......... *G01N 21/8507* (2013.01); *G01N 33/18* (2013.01); *G01N 2021/458* (2013.01); *G01N 2021/8528* (2013.01)

(56) References Cited

U.S. PATENT DOCUMENTS

| | | | |
|---|---|---|---|
| 2014/0185054 A1* | 7/2014 | Atia | G01B 9/02067 356/479 |
| 2014/0293286 A1 | 10/2014 | Kapit et al. | |
| 2017/0003116 A1* | 1/2017 | Yee | G01S 17/34 |
| 2017/0356739 A1* | 12/2017 | Deck | G01B 9/02021 |
| 2017/0357218 A1* | 12/2017 | Sheahan | G04R 20/02 |

FOREIGN PATENT DOCUMENTS

| | | | | |
|---|---|---|---|---|
| CN | 101271241 | | 9/2008 | |
| CN | 102128810 | | 7/2011 | |
| CN | 102151121 | * | 8/2011 | ............... A61B 5/00 |
| CN | 202453113 | | 9/2012 | |
| CN | 102735713 | | 10/2012 | |
| CN | 103743675 | | 4/2014 | |
| CN | 104155246 | | 11/2014 | |
| CN | 104166130 | | 11/2014 | |
| CN | 104434028 | * | 3/2015 | ............... A61B 3/14 |
| CN | 104755908 | * | 7/2015 | ......... G01B 9/02091 |
| CN | 102835948 | * | 3/2016 | ............... A61B 5/00 |
| CN | 105783763 | * | 7/2016 | ............. G01B 11/16 |
| CN | 105891434 | | 8/2016 | |
| CN | 106225816 | * | 12/2016 | ......... G01D 5/35364 |
| CN | 205785095 | * | 12/2016 | ............. G01B 11/16 |
| CN | 106547120 | * | 3/2017 | ............ G02F 1/0121 |
| CN | 107990997 | * | 5/2018 | .............. G01K 11/32 |
| CN | 105910728 | * | 6/2018 | ................ G01N 1/00 |
| CN | 108180930 | * | 6/2018 | ............. G01D 5/353 |
| CN | 110686709 | * | 1/2020 | |
| JP | 2008203129 | | 9/2008 | |
| WO | WO 2010047936 | * | 4/2010 | ......... H01S 3/06791 |
| WO | WO 2014078646 | * | 5/2014 | ......... G01N 15/1429 |

OTHER PUBLICATIONS

Yin Yu et al., "Simulation of simultaneously obtaining ocean temperature and salinity using dual-wavelength Brillouin lidar", Laser Physics Letters, Jan. 23, 2014, pp. 1-7.

"International Search Report (Form PCT/ISA/210)", dated Aug. 23, 2017, with English translation thereof, pp. 1-6.

* cited by examiner

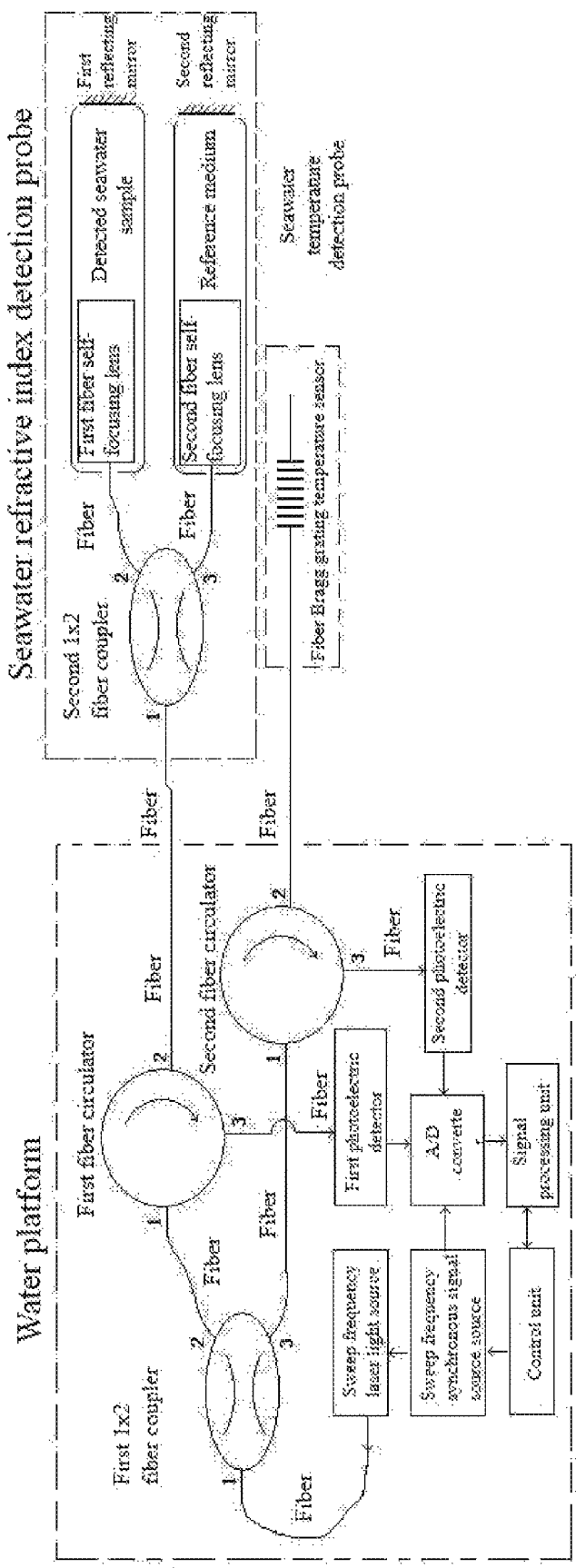

METHOD AND DEVICE FOR ON-LINE DETECTION OF SALINITY OF SEATER

CROSS-REFERENCE TO RELATED APPLICATION

This application is a 371 application of the international PCT application serial no. PCT/CN2017/087086, filed on Jun. 2, 2017, which claims the priority benefit of China application no. 201610394000.3, filed on Jun. 3, 2016. The entirety of each of the abovementioned patent applications is hereby incorporated by reference herein and made a part of this specification.

BACKGROUND OF THE INVENTION

Technical Field

The present invention relates to seawater salinity detection technology, in particular to a method and device for on-line detection of the salinity of seawater.

Description of Related Art

The salinity of seawater is a measurement of the salt content of seawater. Salinity is a basic parameter which reflects the physical process and chemical process of seawater. The real-time on-line detection of the salinity of seawater has a great significance in the fields of marine environment protection, marine science, marine engineering, military and national defense, etc. In recent years, technologies for salinity detection of seawater have been widely highlighted.

In accordance with a Chinese invention patent "Device for Detection of Salinity of Seawater through Multiple Refraction of a Prism Model" (Filing No. of the patent: 201010603445.0), a laser device outputs red light with a wavelength of 650 nm to radiate a reference liquid and a detected liquid; the red light is received by a position sensitive detector (PSD) after being refracted for a plurality of times by a prism; and the salinity value of the liquid is calculated according to the position change information of the PSD. The PSD is a photoelectric device and works with electricity. This invention patent belongs to methods where the seawater measurement terminal (also called wet terminal) is electrified. Therefore, the device is not suitable for long-term on-line detection of the sea.

In accordance with a Chinese invention patent "High-Precision Seawater Salinity Measuring Instrument" (Filing No. of the patent: 201210244182.8), the measured seawater and standard seawater are respectively filled into two different constant-temperature tanks; the electric conductivity of the seawater samples and standard seawater is measured by using components such as a sine-wave generator, a high-precision standard resistor and a voltage transformer; and the salinity value of the seawater is obtained by converting the electric conductivity ratio of the seawater samples to the standard seawater. By using this method, a sine-wave voltage needs to be applied to an electrode of each of the constant-temperature tanks, and the constant-temperature tanks work with electricity, which means that this method also belongs to methods where the seawater measurement terminal (wet terminal) is electrified. Therefore, this method applies to indoor detection only, and cannot apply to the on-line detection of the sea.

In accordance with a Chinese invention patent "Device and Method for On-line Detection of Salinity of Seawater" (Filing No. of the patent: 201410425894.9), resonance is generated in an annular cavity of a micro-nanofiber through mutual interaction between a strong evanescent field of the micro-nanofiber and seawater, and the salinity value of the seawater is calculated with an equation on the basis of the resonance wavelength. This patented technology is advanced in its detection principle, and has good prospects for application. However, a spectrum analyzer is required to scan and obtain a spectrogram of the measured seawater and to read the wavelength of the resonance peak of the measured seawater. Therefore, this patented technology is disadvantaged in high implementation cost and relatively large equipment size.

A Chinese invention patent "Method for Synchronously Inverting Seawater Temperature and Salinity by Brillouin Frequency Shift and Line Width" (Filing No. of the patent: 201410386610.X) only discloses the calculation equation and the inversion method of the Brillouin frequency shift and the line width under the conditions of a certain temperature and salinity of seawater, and does not involve the design of a method and device for measuring the temperature and salinity of seawater.

In conclusion, the existing technologies for the detection of the salinity of seawater have various technical defects and are particularly not suitable for long-term on-line monitoring of the sea.

BRIEF SUMMARY OF THE INVENTION

In order to solve the problems of the prior art, the present invention provides a method and device for on-line detection of the salinity of seawater. A sweep frequency synchronous signal controls a sweep frequency laser light source such that the wavelength of the frequency modulation light wave output by the sweep frequency laser light source is a periodic saw-tooth wave signal. The frequency modulation light wave is divided into two beams, respectively transmitted to a refractive index probe and a temperature probe in seawater. The refractive index probe is an interference instrument structure, and the frequency value of an interference light intensity signal fed back by the refractive index probe is related to the refractive index of the seawater. The refractive index of the seawater is calculated by performing discrete Fourier transformation on the interference light intensity signal. The temperature probe is internally provided with a fiber Bragg grating, and the Bragg wavelength of the reflection spectrum of the temperature probe is related to the temperature of the seawater. The sweep frequency synchronous signal and the reflection light intensity signal of the fiber Bragg grating are subjected to synchronous discrete sampling, and the temperature value of the seawater is calculated according to a grating temperature sensor demodulation algorithm. The salinity value of the detected seawater is obtained by solving an empirical equation according to the obtained refractive index, the temperature value, and the average wavelength of the frequency modulation light wave, thereby implementing on-line detection of the salinity of the seawater. The fiber Bragg Grating is usually called FBG for short in the literature.

The beneficial effect of the invention is as follows.

I. The phase fading phenomenon can be effectively avoided by adopting a frequency modulation light wave of which the wavelength presents periodic saw-tooth wave changes. The refractive index detection probe is an interference instrument structure; a sensor arm of the interference instrument is mainly comprised of samples of the detected seawater and a reflecting mirror; a reference arm of the interference instrument is mainly comprised of a medium of which the refractive index is known and a reflecting mirror; the sensor arm and the reference arm are equal in length; the frequency modulation light wave entering the refractive index detection probe forms sensing light and reference light by the effect of the interference instrument; the sensing light and the reference light form interference light by the interference effect, and the interference light is fed back by the refractive index detection probe.

According to the principle that two light beams interfere with each other, the interference light intensity signal I(t) fed back by the refractive index detection probe is:

$$I(t)=I_S+I_R+2\sqrt{I_S I_R}\cos(\Delta\phi) \quad (1);$$

where t is a time variable, $I_S$ and $I_R$ are respectively the sensing light intensity and reference light intensity of the interference instrument, $I_S \geq 0$, $I_R \geq 0$, and $\Delta\phi$ is the phase difference between the sensing light and reference light of the interference instrument. The sensor arm and the reference arm are equal in length, so the phase difference $\Delta\phi$ is:

$$\Delta\phi = \frac{4\pi l(n_S - n_R)}{\lambda(t)}; \quad (2)$$

where l is the length of the sensor arm and the reference arm, $n_S$ and $n_R$ are respectively the to-be-detected refractive index of the seawater and the known refractive index of the reference medium, and $\lambda(t)$ is the wavelength of the light wave output by the laser light source.

If the laser light source outputs the light wave with a fixed wavelength, namely $\lambda(t)=\lambda_0$, where $\lambda(t)=\lambda_0$ is a constant, then according to equation (1) and equation (2), the interference light intensity I(t) fed back by the refractive index detection probe is:

$$I(t) = I_S + I_R + 2\sqrt{I_S I_R} \cos\left[\frac{4\pi l(n_S - n_R)}{\lambda_0}\right]; \quad (3)$$

where if the changes of the $I_S$, $I_R$ and $n_R$ that occur along with the time are neglected, the differential $$\frac{dI(t)}{dt}$$

of the interference light intensity I(t) to time is:

$$\frac{dI(t)}{dt} = -2\sqrt{I_S I_R}\left\{\sin\left[\frac{4\pi l(n_S - n_R)}{\lambda_0}\right]\right\}\frac{4\pi l}{\lambda_0}\frac{dn_S}{dt}; \quad (4)$$

where $$\frac{dn_S}{dt}$$

is the differential of the refractive index of the seawater to time.

From equation (4) it is known that, when $$\frac{4\pi l(n_S - n_R)}{\lambda_0} = m\pi,$$

where m is an integer, the following equation is satisfied:

$$\frac{dI(t)}{dt} = 0.$$

The above means that, when the laser light source outputs the light wave with a fixed wavelength $\lambda_0$, and when $$\frac{4\pi l(n_S - n_R)}{\lambda_0} = m\pi,$$

the differential $$\frac{dI(t)}{dt}$$

of the interference light intensity I(t) to time is zero, and I(t) never varies with the refractive index $n_S$ of the seawater, even if the refractive index $n_S$ of the seawater changes along with the time, namely $$\frac{dn_S}{dt} \neq 0.$$

At this time, the refractive index detection probe works in the most insensitive area, and the so-called phase fading phenomenon appears. Therefore, technical means must be taken to avoid the influence of the phase fading phenomenon and to accurately implement sensing of the physical quantity.

A sweep frequency laser light source is adopted to output the frequency modulation light wave of which the wavelength $\lambda(t)$ is a saw-tooth wave signal with a sweep frequency period T. The specific form is as follows:

$$\lambda(t) = \begin{cases} \lambda_0 + \dfrac{2\Delta\lambda}{T}(t-nT) & nT \leq t \leq nT + \dfrac{T}{2} \\ \lambda_0 + \dfrac{2\Delta\lambda}{T}(nT+T-t) & nT + \dfrac{T}{2} \leq t \leq (n+1)T \end{cases} \quad (5)$$

where t is a time variable; n is a nonnegative integer; $\lambda_0$ is the start or end time of the wavelength $\lambda(t)$ in every sweep frequency period T, namely a wavelength value corresponding to t=nT or t=(n+1)T, while $\lambda_0$ is the minimum wavelength in the sweep frequency process; when $\Delta\lambda>0$, $\Delta\lambda$ is the variation range of the wavelength during sweep frequency; $\lambda_0+\Delta\lambda$ is the middle time of $\lambda(t)$ in each sweep frequency period, namely a wavelength value corresponding to $$t = nT + \frac{T}{2};$$

and $\lambda_0+\Delta\lambda$ is the maximum wavelength in the sweep frequency process.

$$\frac{1}{\lambda(t)} = \begin{cases} \dfrac{1}{\lambda_0 + \dfrac{2\Delta\lambda}{T}(t-nT)} & nT \leq t \leq nT + \dfrac{T}{2} \\ \dfrac{1}{\lambda_0 + \dfrac{2\Delta\lambda}{T}(nT+T-t)} & nT + \dfrac{T}{2} \leq t \leq (n+1)T \end{cases} \quad (6)$$

$$\frac{1}{\lambda(t)} = \begin{cases} \dfrac{1}{\lambda_0}\left[\dfrac{1}{1+\dfrac{2\Delta\lambda}{T\lambda_0}(t-nT)}\right] & nT \leq t \leq nT + \dfrac{T}{2} \\ \dfrac{1}{\lambda_0}\left[\dfrac{1}{1+\dfrac{2\Delta\lambda}{T\lambda_0}(nT+T-t)}\right] & nT + \dfrac{T}{2} \leq t \leq (n+1)T \end{cases} \quad (7)$$

If $\Delta\lambda \ll \lambda_0$, by using series expansion, while the higher order small terms are neglected:

$$\frac{1}{\lambda(t)} = \begin{cases} \frac{1}{\lambda_0}\left[1 - \frac{2\Delta\lambda}{T\lambda_0}(t - nT)\right] & nT \le t \le nT + \frac{T}{2} \\ \frac{1}{\lambda_0}\left[1 - \frac{2\Delta\lambda}{T\lambda_0}(nT + T - t)\right] & nT + \frac{T}{2} \le t \le (n+1)T \end{cases} \quad (8)$$

Substitute Equation (8) into equation (2):

$$\Delta\phi = \begin{cases} \frac{4\pi l(n_S - n_R)}{\lambda_0}\left[1 - \frac{2\Delta\lambda}{T\lambda_0}(t - nT)\right] & nT \le t \le nT + \frac{T}{2} \\ \frac{4\pi l(n_S - n_R)}{\lambda_0}\left[1 - \frac{2\Delta\lambda}{T\lambda_0}(nT + T - t)\right] & nT + \frac{T}{2} \le t \le (n+1)T \end{cases} \quad (9)$$

Substitute Equation (9) into equation (1):

$$I(t) = \begin{cases} I_S + I_R + 2\sqrt{I_S I_R}\cos\left[\frac{4\pi l(n_S - n_R)}{\lambda_0}\left(1 - \frac{2\Delta\lambda(t - nT)}{T\lambda_0}\right)\right] & nT \le t \le nT + \frac{T}{2} \\ I_S + I_R + 2\sqrt{I_S I_R}\cos\left[\frac{4\pi l(n_S - n_R)}{\lambda_0}\left(1 - \frac{2\Delta\lambda(nT - t)}{T\lambda_0}\right)\right] & nT + \frac{T}{2} \le t \le (n+1)T \end{cases} \quad (10)$$

If the changes of the $I_S$ and $I_R$ in one sweep frequency period T are neglected, $I_S$ and $I_R$ within one sweep frequency period T are regarded as constants, then the interference light intensity signal I(t) is the sum of a DC component $I_{DC}$ and an AC component $I_{AC}(t)$:

$$I(t) = I_{DC} + I_{AC}(t) \quad (11);$$

where the DC component $I_{DC}$ of the interference light intensity signal I(t) is:

$$I_{DC} = I_S + I_R \quad (12)$$

the AC component $I_{AC}(t)$ of the interference light intensity signal I(t) is:

$$I_{AC}(t) = \begin{cases} 2\sqrt{I_S I_R}\cos\left[\frac{4\pi l(n_S - n_R)}{\lambda_0}\left(1 - \frac{2\Delta\lambda(t - nT)}{T\lambda_0}\right)\right] & nT \le t \le nT + \frac{T}{2} \\ 2\sqrt{I_S I_R}\cos\left[\frac{4\pi l(n_S - n_R)}{\lambda_0}\left(1 - \frac{2\Delta\lambda(nT - t)}{T\lambda_0}\right)\right] & nT + \frac{T}{2} \le t \le (n+1)T \end{cases} \quad (13)$$

In the above equation, $\lambda_0$, $\Delta\lambda$, l and $n_R$ are constants. The refractive index $n_S$ of the seawater usually changes relatively slowly, so $n_S$ may also be regarded as a constant within one sweep frequency period T, and then the AC component $I_{AC}(t)$ within one sweep frequency period T is a single-frequency signal, with a frequency value $\omega_s$ $$\omega_s = \frac{8\pi(n_S - n_R)l}{\lambda_0}\frac{\Delta\lambda}{\lambda_0 T}. \quad (14)$$

Thus, it can be seen that the frequency value $\omega_s$ of the AC component $I_{AC}(t)$ within one sweep frequency period T is related to the refractive index $n_S$ of the seawater.

Equation (14) is converted to obtain the following equation:

$$n_S - n_R = \omega_s T \frac{\lambda_0^2}{8\pi\Delta\lambda l},$$

$$n_S = n_R + \frac{\omega_s T \lambda_0^2}{8\pi\Delta\lambda l}. \quad (15)$$

Through performing discrete Fourier transformation on the interference light intensity signal I(t), a frequency value $\omega_s$ is obtained. The refractive index $n_S$ of the seawater can be calculated with the equation (15). Therefore, when the sweep frequency laser light source is adopted to output the frequency modulation light wave, the influences of the phase fading phenomenon can be effectively avoided, and the detection of the refractive index of the seawater can be accurately implemented.

In addition, the wavelength continuously changes in the form of a periodic saw-tooth wave. With respect to the periodic square waveform, the output change of the laser light source is smooth, and the performance is more stable.

II. By adopting the frequency modulation light wave of which the wavelength changes in the form of a periodic saw-tooth wave, the fiber Bragg grating conveniently implements temperature sensing demodulation.

The temperature probe is internally provided with a fiber Bragg grating, and the Bragg wavelength of the reflection spectrum of the temperature probe is related to the temperature value of the seawater. The sweep frequency synchronous signal and the reflection light intensity signal of the fiber Bragg grating are subjected to synchronous discrete sampling to obtain the reflection spectrum at the current temperature. The corresponding Bragg wavelength is obtained with the maximum value in the reflection spectrum and the corresponding sweep frequency synchronous signal voltage value. Then, the current temperature value of the seawater is calculated according to the characteristic parameters of the fiber Bragg grating temperature sensor. Therefore, by adopting the frequency modulation light wave of which the wavelength changes in the form of a periodic saw-tooth wave, the fiber Bragg grating conveniently implements temperature sensing demodulation.

III. The salinity value of the seawater is calculated by solving an empirical equation.

The salinity value of the detected seawater is obtained by solving an empirical equation according to the obtained refractive index, the temperature value and the average wavelength of the frequency modulation light wave, thereby implementing on-line detection of the salinity of seawater. Reference: Xiaohong Quan and Edward S. Fry. Empirical equation for the index of refraction of seawater, APPLIED OPTICS [J]. 1995. Vol. 34, No. 18:3477-3480. The specific form of the empirical equation is as follows:

$$n_S = n_0 + (n_1 + n_2 T_S + n_3 T_S^2)S + n_4 T_S^2 + \frac{n_5 + n_6 S + n_7 T_S}{\bar{\lambda}} + \frac{n_8}{\bar{\lambda}^2} + \frac{n_9}{\bar{\lambda}^3} \quad (16)$$

where the respective coefficients are as follows:
$n_0 = 1.31405$, $n_1 = 1.779 \times 10^{-4}$, $n_2 = -1.05 \times 10^{-6}$, $n_3 = 1.6 \times 10^{-8}$, $n_4 = -2.02 \times 10^{-6}$, $n_5 = 15.868$, $n_6 = 0.01155$, $n_7 = -0.00423$, $n_8 = -4382$, $n_9 = 1.1455 \times 10^6$.

In the above empirical equation, the refractive index of the seawater is used as the function of the salinity value and the temperature value of the seawater and the average wavelength of the light wave. The reference shows that the calculation results are well tallied with the experimental data, and the accuracy is reliable.

IV. The present invention belongs to the method where the seawater measurement terminal (wet terminal) is completely chargeless.

A device for on-line detection of the salinity of seawater of the present invention includes a water platform, a seawater refractive index detection probe and a seawater temperature detection probe. The water platform works with electricity, and the two types of detection probes placed in seawater are both comprised of optical passive devices, and do not need electricity. The probes are connected with the water platform through two fibers, without any electrical connection with the water platform. The present invention belongs to the method where the seawater measurement terminal (wet terminal) is completely chargeless. The present invention has the features of anti-leakage, anti-corrosion, simple installation and convenient maintenance, and is more suitable for on-line detection of the salinity of seawater in the outdoor environment.

BRIEF DESCRIPTION OF THE SEVERAL VIEWS OF THE DRAWINGS

FIG. 1 is a structural view of a device for on-line detection of the salinity of seawater of the present invention.

DETAILED DESCRIPTION OF THE INVENTION

The present invention is described in detail below in conjunction with the attached drawings.

Embodiment 1

A method for on-line detection of the salinity of seawater includes the following steps:

Step 1: Controlling a sweep frequency synchronous signal source to ensure a sweep frequency synchronous signal $V(t)$ output by the sweep frequency synchronous signal source is a saw-tooth wave voltage signal with a sweep frequency period T, where the specific form is as follows:

$$V(t) = \begin{cases} V_0 + \frac{2(V_P - V_0)}{T}(t - nT) & nT \le t \le nT + \frac{T}{2} \\ V_P + \frac{2(V_P - V_0)}{T}\left(nT + \frac{T}{2} - t\right) & nT + \frac{T}{2} \le t \le nT + T \end{cases}$$

where t is a time variable, n is a nonnegative integer, n=0 1 2, ..., $V_0$ is the start or end time of $V(t)$ in each sweep frequency period T, namely a voltage value corresponding to t=nT or t=(n+1)T, while $V_P$ is the middle time of $V(t)$ in each sweep frequency period, namely a voltage value corresponding to $$t = nT + \frac{T}{2},$$

$V_0 \ge 0$, and $V_P > V_0$.

Step 2: By the effect of the sweep frequency synchronous signal source, the wavelength $\lambda(t)$ of the frequency modulation light wave output by the sweep frequency laser light source linearly varies with the sweep frequency synchronous signal $V(t)$, where the wavelength $\lambda(t)$ is a saw-tooth wave signal with a sweep frequency period T, and the specific form is as follows:

$$\lambda(t) = \begin{cases} \lambda_0 + \frac{2\Delta\lambda}{T}(t - nT) & nT \le t \le nT + \frac{T}{2} \\ \lambda_0 + \frac{2\Delta\lambda}{T}(nT + T - t) & nT + \frac{T}{2} \le t \le (n+1)T \end{cases}$$

where $\lambda_0$ is the start or end time of the wavelength $\lambda(t)$ in each sweep frequency period T, namely a wavelength value corresponding to t=nT or t=(n+1)T, while $\lambda_0$ is the minimum wavelength in the sweep frequency process, $\Delta\lambda>0$, $\Delta\lambda$ is the sweep frequency variation range of the wavelength, $\lambda_0+\Delta\lambda$ is the middle time of $\lambda(t)$ in each sweep frequency period, namely a wavelength value corresponding to $$t = nT + \frac{T}{2},$$

and $\lambda_0+\Delta\lambda$ is the maximum wavelength in the sweep frequency process.

Step 3: The frequency modulation light wave output by the sweep frequency laser light source is divided into two beams of light, and transmitted the two beams of light into a refractive index detection probe and a temperature detection probe that are placed in the detected seawater, by a wave guide, where the refractive index detection probe is an interference instrument structure, a sensor arm of the interference instrument is mainly comprised of samples of the detected seawater and a first reflecting mirror, a reference arm of the interference instrument is mainly comprised of a reference medium of which the refractive index is known and a second reflecting mirror, the sensor arm and the reference arm are equal in length, namely length l, the light entering the refractive index probe forms sensing light and reference light by the effect of the interference instrument, the sensing light and the reference light form interference light by the interference effect, and the interference light is fed back by the refractive index probe; where the temperature detection probe is internally provided with a fiber Bragg grating temperature sensor, the frequency modulation light wave entering the temperature sensor forms reflection light and a reflection spectrum by the effect of the fiber Bragg grating temperature sensor, and the Bragg wavelength of the reflection spectrum is related to the temperature value of seawater, so the reflection light is called temperature reflection light; where the temperature detection probe is internally provided with a fiber Bragg grating temperature sensor; the Bragg wavelength of the reflection spectrum of the temperature detection probe varies along with the temperature change of the seawater; and within the whole temperature change range of the seawater, the variation range of the Bragg wavelength of the temperature detection probe does not exceed the sweep frequency wavelength range of the sweep frequency laser light source, which means that the Bragg wavelength varies between $\lambda_0$ and $\lambda_0+\Delta\lambda$.

Step 4: The interference light intensity signal $I(t)$ and a temperature reflection light intensity signal $G(t)$ are measured with a photoelectric detector, where the whole measurement time is divided into a plurality of measurement time segments equal in length, the length of each time segment is two sweep frequency periods, namely 2T, the interference light intensity signal $I(t)$ is measured in the first sweep frequency period T of each time segment, and the temperature reflection light intensity G(t) is measured in the second sweep frequency period T of the same time segment; where the interference light intensity I(t) is:

$$I(t) = \begin{cases} I_S + I_R + 2\sqrt{I_S I_R} \cos\left[\dfrac{4\pi l(n_S - n_R)}{\lambda_0}\left(1 - \dfrac{2\Delta\lambda(t - nT)}{T\lambda_0}\right)\right] & nT \le t \le nT + \dfrac{T}{2} \\ I_S + I_R + 2\sqrt{I_S I_R} \cos\left[\dfrac{4\pi l(n_S - n_R)}{\lambda_0}\left(1 - \dfrac{2\Delta\lambda(nT - t)}{T\lambda_0}\right)\right] & nT + \dfrac{T}{2} \le t \le (n+1)T \end{cases}$$

where $I_S$ and $I_R$ are respectively the sensing light intensity and reference light intensity of the interference instrument; if the changes of the $I_S$ and $I_R$ in one sweep frequency period T are neglected, $I_S$ and $I_R$ within one sweep frequency period T are regarded as constants, and then the interference light intensity I(t) is the sum of a DC component $I_{DC}$ and an AC component $I_{AC}(t)$:

$$I(t) = I_{DC} + I_{AC}(t)$$

where the DC component $I_{DC}$ of the interference light intensity I(t) is:

$$I_{DC} = I_S + I_R$$

the AC component $I_{AC}(t)$ of the $I_{AC}(t)$ is:

$$I_{AC}(t) = \begin{cases} 2\sqrt{I_S I_R} \cos\left[\dfrac{4\pi l(n_S - n_R)}{\lambda_0}\left(1 - \dfrac{2\Delta\lambda(t - nT)}{T\lambda_0}\right)\right] & nT \le t \le nT + \dfrac{T}{2} \\ 2\sqrt{I_S I_R} \cos\left[\dfrac{4\pi l(n_S - n_R)}{\lambda_0}\left(1 - \dfrac{2\Delta\lambda(nT - t)}{T\lambda_0}\right)\right] & nT + \dfrac{T}{2} \le t \le (n+1)T \end{cases}$$

in the above equation, $\lambda_0$, $\Delta\lambda$, l and $n_R$ are constants; the refractive index $n_S$ of the seawater usually changes relatively slowly, so $n_S$ may also be regarded as a constant within one sweep frequency period T, and then the AC component $I_{AC}(t)$ within one sweep frequency period T is a single-frequency signal, with a frequency value $\omega_s$:

$$\omega_s = \dfrac{8\pi(n_S - n_R)l}{\lambda_0} \dfrac{\Delta\lambda}{\lambda_0 T}.$$

Step 5: First, n=0 is defined, and the start time of the current time segment is set to be t=nT.

Step 6: From the time t=nT, discrete sampling is carried out on the interference light intensity I(t) signal in the first sweep frequency period T of the current time segment in a sampling period $T_1$ by using an A/D converter to obtain a sampling signal sequence I(m) in the first sweep frequency period $T_1$, namely from the time t=nT to the time t=(n+1)T, wherein the length of the sequence is $L_1$, m is the sequence number and is a nonnegative integer, m=0, 1, 2 ... $L_1-1$; and I(m) is saved in a signal processing unit; where the sampling period T is required to meet the requirements of a sampling theorem, namely the following condition:

$$T_1 < \dfrac{2\pi}{2\omega_s} = \dfrac{\lambda_0^2 T}{8(n_S - n_R)l\Delta\lambda},$$

and the length $L_1$ of the sampling signal sequence I(m) is:

$$L_1 = \dfrac{T}{T_1}.$$

Step 7: From the time t=(n+1)T, discrete sampling is carried out on the sweep frequency synchronous signal V(t) and temperature reflection light intensity G(t) in the second sweep frequency period T of the current time segment in a sampling period $T_2$ by using the A/D converter to obtain a sweep frequency synchronous signal sequence V(h) and a temperature reflection light intensity sequence G(h) in the second sweep frequency period T, namely from the time t=(n+1)T to the time t=(n+2)T, wherein the lengths of the sequences V(h) and G(h) are equal, namely $L_2$, h is the sequence number and is a nonnegative integer, h=0 1 2 ... $L_2-1$; and V(h) and G(h) are saved in the signal processing unit;

where the sampling period $T_2$ is $$T_2 = \dfrac{T}{1024};$$

the lengths of the sweep frequency synchronous signal sequence V(h) and the temperature reflection light intensity signal sequence G(h) are both $L_2$, and $L_2$ is $$L_2 = \dfrac{T}{T_2} = 1024.$$

Step 8: FFT (Fast Fourier Transformation) is carried out on the interference light intensity sampling signal sequence I(m) in the first sweep frequency period T of the current time segment by the signal processing unit to obtain a spectrum distribution of the interference light intensity I(t) in the current time, and the frequency value $\omega_s$ of an alternating current component $I_{AC}(t)$ of the interference light intensity I(t) in the above mentioned time is calculated according to the frequency spectrum distribution.

Step 9: In accordance with the relation between the frequency value $\omega_s$ of the alternating current component $I_{AC}(t)$ of the interference light intensity and the index of reflection $n_S$ of seawater, the index of refraction $n_S$ of the samples of the detected seawater in the first sweep frequency period T, namely from the time t=nT to the time t=(n+1)T, of the current time segment is calculated by using the following equation:

$$n_S = n_R + \dfrac{\omega_s T \lambda_0^2}{8\pi\Delta\lambda l}$$

where l represents the lengths of the sensor arm and the reference arm of the refractive index detection probe, and $n_R$ is the known refractive index of the reference medium of the probe.

Step 10: By using the sweep frequency synchronous signal sequence V(h) and the temperature reflection light intensity signal sequence G(h) in the second sweep frequency period T of the current time segment, the temperature value $T_S$ of the detected seawater in the second sweep frequency period T, namely from the time t=(n+1)T to the time t=(n+2)T is calculated and obtained according to a fiber Bragg grating temperature sensor demodulation algorithm; where the fiber Bragg grating temperature sensor demodulation algorithm includes the following steps:

First, finding the maximum temperature reflection light intensity value G(h_M) and the corresponding sequence number h_M according to the temperature reflection light intensity signal sequence G(h);

second, finding the sweep frequency synchronous signal voltage value V(h_M) at this moment according to the sequence number h_M corresponding to the maximum temperature reflection light intensity value G(h_M).

third, finding the Bragg wavelength of the fiber grating temperature sensor corresponding to the maximum temperature reflection light intensity value G(h_M) according to the sweep frequency synchronous signal voltage value V(h_M) corresponding to the sequence number h_M; and, fourth, according to the characteristic parameters of the fiber Bragg grating temperature sensor, calculating the current seawater temperature value $T_S$ on the basis of the maximum temperature reflection light intensity value G(h_M).

Step 11: Changes of the refractive index $n_S$ and the temperature $T_S$ of the seawater in each measurement time segment can be neglected because the refractive index $n_S$ and the temperature $T_S$ of the seawater change relatively slowly, wherein each measurement time segment includes two sweep frequency periods; the reflective indexes $n_S$ of the seawater samples obtained in the first sweep frequency period T of the time segment, namely from the time t=nT to the time t=(n+1)T, are approximated as the refractive index $n_S$ of the seawater samples in the whole time segment, namely from the time t=nT to the time t=(n+2)T; similarly, the temperature values $T_S$ of the seawater obtained in the second sweep frequency period T of the time segment, namely from the time t=(n+1)T to the time t=(n+2)T, are approximated as the temperature value $T_S$ of the seawater in the whole time segment, namely from the time t=nT to the time t=(n+2)T.

Step 12: The following empirical equation is solved according to the obtained reflective index $n_S$ and the temperature value $T_S$ of the seawater and the average wavelength $\bar{\lambda}$ $$\left(\bar{\lambda} = \lambda_0 + \frac{\Delta\lambda}{2}\right)$$

output by the sweep frequency laser light source in the current time segment:

$$n_S = n_0 + (n_1 + n_2 T_S + n_3 T_S^2)S + n_4 T_S^2 + \frac{n_5 + n_6 S + n_7 T_S}{\bar{\lambda}} + \frac{n_8}{\bar{\lambda}^2} + \frac{n_9}{\bar{\lambda}^3}$$

the salinity S of the seawater in the current time segment, namely from the time t=nT to the time t=(n+2)T is calculated, wherein respective coefficients are as follows: $n_0$=1.31405, $n_1$=1.779×10$^{-4}$, $n_2$=−1.05×10$^{-6}$, $n_3$=1.6×10$^{-8}$, $n_4$=−2.02×10$^{-6}$, $n_5$=15.868, $n_6$=0.01155, $n_7$=−0.00423, $n_8$=−4382, $n_9$=1.1455×10$^6$.

Step 13: n=n+2 is defined, the start time of the time segment is updated and pointed at the next time segment.

Step 14: Steps 6-13 are repeated in a circular way; the salinity S of the seawater in any time segment after the start time t=0, namely from the time t=nT to the time t=(n+2)T is measured thus implementing real-time detection of the salinity of seawater, wherein n=0 1 2, . . . .

Embodiment 2

A device for on-line detection of the salinity of seawater for the method for on-line detection of the salinity of seawater in Embodiment 1 includes a water platform, a seawater refractive index detection probe and a seawater temperature detection probe. The water platform is respectively connected with the seawater refractive index detection probe and the seawater temperature detection probe through two fibers. The water platform outputs the frequency modulation light wave of which the wavelength is a periodic saw-tooth wave signal. The frequency modulation light wave is divided into two beams which are respectively transmitted to a refractive index probe and a temperature probe in seawater; the refractive index probe is an interference instrument structure, and the temperature probe is internally provided with a fiber Bragg grating.

The water platform includes a sweep frequency laser light source, a sweep frequency synchronous signal source, a first photoelectric detector, a second photoelectric detector, an A/D converter, a signal processing unit, a control unit, a first 1×2 fiber coupler, a first fiber circulator and a second fiber circulator. The seawater temperature detection probe includes a fiber Bragg grating temperature sensor. The sweep frequency laser light source is provided with a fiber interface and an electrical interface. The sweep frequency laser light source is connected with the sweep frequency synchronous signal source through the electrical interface. The sweep frequency laser light source is connected with an arm 1 of the first 1×2 fiber coupler through the fiber interface. An arm 2 and an arm 3 of the first 1×2 fiber coupler are respectively connected with an arm 1 of the first fiber circulator and an arm 1 of the second fiber circulator. An arm 2 and an arm 3 of the first fiber circulator are respectively connected with the refractive index detection probe and the first photoelectrical detector. An arm 2 and an arm 3 of the second fiber circulator are respectively connected with the seawater temperature detection probe and the second photoelectric detector. The sweep frequency synchronous signal source, the first photoelectric detector and the second photoelectric detector all are connected with the A/D converter. The A/D converter is connected with a signal processing unit. The signal processing unit is connected with a control unit. The control unit is also connected with a sweep frequency synchronous signal source.

The refractive index detection probe includes a second 1×2 fiber coupler, a first fiber self-focusing lens, a second fiber self-focusing lens, a seawater sample cavity, a reference medium, a first reflecting mirror and a second reflecting mirror. An arm 1 of the second 1×2 fiber coupler is connected with the arm 2 of the first fiber circulator; an arm 2 and an arm 3 of the second 1×2 fiber coupler are respectively connected with the first fiber self-focusing lens and the second fiber self-focusing lens. The seawater sample cavity is positioned between the first fiber self-focusing lens and the first reflecting mirror. The reference medium is positioned between the second fiber self-focusing lens and the second reflecting mirror.

The above are detailed descriptions of the present invention in conjunction with specific preferable embodiments, but it cannot be regarded that the specific embodiments of the present invention are limited to the above description. For those ordinarily skilled in the art, various simple modifications or replacements can be made on the basis of the concept of the present invention, which shall all fall within the protective scope of the present invention.

What is claimed is:

1. A method for on-line detection of the salinity of seawater, comprising the following steps:
    step 1: controlling a sweep frequency synchronous signal source to ensure a sweep frequency synchronous signal V(t) output by a sweep frequency synchronous signal source is a saw-tooth wave voltage signal with a sweep frequency period T, wherein a specific form of the sweep frequency synchronous signal is as follows:

$$V(t) = \begin{cases} V_0 + \dfrac{2(V_P - V_0)}{T}(t - nT) & nT \le t \le nT + \dfrac{T}{2} \\ V_P + \dfrac{2(V_P - V_0)}{T}\left(nT + \dfrac{T}{2} - t\right) & nT + \dfrac{T}{2} \le t \le nT + T \end{cases}$$

wherein, t is a time variable, n is a nonnegative integer, n=0, 1 2, ..., $V_0$ is a start or end time of V(t) in each of the sweep frequency period T, namely a voltage corresponding to t=nT or t=(n+1)T, while $V_P$ is the V(t) in the middle of each of the sweep frequency period, namely a voltage corresponding to $$t = nT + \frac{T}{2},$$

$V_0 \ge 0$, and $V_P > V_0$;

step 2: by an effect of the sweep frequency synchronous signal source, controlling the wavelength λ(t) of a frequency modulation light wave output by a sweep frequency laser light source to linearly vary with the sweep frequency synchronous signal V(t), wherein the wavelength λ(t) is also a saw-tooth wave voltage signal with the sweep frequency period T, and a specific form of the wavelength λ(t) is as follows:

$$\lambda(t) = \begin{cases} \lambda_0 + \dfrac{2\Delta\lambda}{T}(t - nT) & nT \le t \le nT + \dfrac{T}{2} \\ \lambda_0 + \dfrac{2\Delta\lambda}{T}(nT + T - t) & nT + \dfrac{T}{2} \le t \le (n+1) + T \end{cases}$$

wherein, $\lambda_0$ is the start or end time of the wavelength λ(t) in each of the sweep frequency period T, namely a wavelength corresponding to t=nT or t=(n+1)T, and $\lambda_0$ is the minimum wavelength in the sweep frequency process, Δλ>0, Δλ is the sweep frequency variation range of the wavelength, $\lambda_0 + \Delta\lambda$ is the λ(t) in the middle of each of the sweep frequency period, namely a wavelength corresponding to $$t = nT + \frac{T}{2},$$

and $\lambda_0 + \Delta\lambda$ is the maximum wavelength in the sweep frequency process;

step 3: dividing the frequency modulation light wave output by the sweep frequency laser light source into two beams of light, and transmitting the two beams of light into a refractive index detection probe and a temperature detection probe that are placed in seawater being tested, by a wave guide, wherein the refractive index detection probe is an interferometer, a sensor arm of the interferometer comprises of samples of the seawater and a first reflecting mirror, a reference arm of the interferometer is mainly comprised of a reference medium of which the refractive index is known and a second reflecting mirror, the sensor arm and the reference arm are equal in length, namely length l, the light entering the refractive index detection probe forms a sensing light and a reference light by the effect of the interferometer, the sensing light and the reference light form an interference light by an interference effect, and the interference light is fed back by the refractive index detection probe; wherein the temperature detection probe comprises a fiber Bragg grating temperature sensor internally, the frequency modulation light wave entering a temperature detection sensor forms the reflection light and a reflection spectrum by the fiber Bragg grating temperature sensor, and the Bragg wavelength of the reflection spectrum is related to the temperature of the seawater, so the reflection light is called a temperature reflection light;

step 4: measuring an interference light intensity I(t) and a temperature reflection light intensity G(t) with a photoelectric detector, wherein a whole measurement time is divided into a plurality of measurement time segments equal in length, the length of each time segment is two sweep frequency periods, namely 2T, the interference light intensity I(t) is measured in a first sweep frequency period T of each time segment, and the temperature reflection light intensity G(t) is measured in the second sweep frequency period T of the same time segment;

step 5: first defining n=0, and setting the start time of the current time segment to be t=nT;

step 6: from the time t=nT, performing a discrete sampling on the interference light intensity I(t) in the first sweep frequency period T of the current time segment in a sampling period $T_1$ by using an A/D converter to obtain a sampling signal sequence I(m) in the first sweep frequency period $T_1$, namely from the time t=nT to the time t=(n+1)T, wherein the length of the sequence is $L_1$, m is a sequence number and is a nonnegative integer, m=0 1 2 . . . $L_1$−1; and saving I(m) in a signal processing unit;

step 7: from the time t=(n+1)T, performing the discrete sampling on the sweep frequency synchronous signal V(t) and the temperature reflection light intensity G(t) in the second sweep frequency period T of the current time segment in a sampling period $T_2$ by using the A/D converter to obtain a sweep frequency synchronous signal sequence V(h) and a temperature reflection light intensity sequence G(h) in the second sweep frequency period T, namely from the time t=(n+1)T to the time t=(n+2)T, wherein the lengths of the sequences V(h) and G(h) are equal, namely $L_2$, h is the sequence number and is a nonnegative integer, h=0 1 2 . . . $L_2$−1; and saving V(h) and G(h) in the signal processing unit;

step 8: performing FFT (Fast Fourier Transformation) on an interference light intensity sampling signal sequence I(m) in the first sweep frequency period T of the current time segment by the signal processing unit to obtain a spectrum distribution of the interference light intensity I(t) in the current time, and calculating the frequency $\omega_s$ of an alternating current component $I_{AC}(t)$ of the interference light intensity I(t) in the above mentioned time according to the frequency spectrum distribution;

step 9: in accordance with the relation between the frequency $\omega_s$ of the alternating current component $I_{AC}(t)$ of the interference light intensity and the reflection index $n_S$ of seawater, calculating the refraction index $n_S$ of the samples of the seawater in the first sweep frequency period T, namely from the time t=nT to the time t=(n+1)T, of the current time segment by using the following equation:

$$n_S = n_R + \frac{\omega_s T \lambda_0^2}{8\pi \Delta \lambda l}$$

wherein l represents the lengths of the sensor arm and the reference arm of the refractive index detection probe, and $n_R$ is a refractive index of the reference medium of the probe;

step 10: by using the sweep frequency synchronous signal sequence V(h) and the temperature reflection light intensity signal sequence G(h) in the second sweep frequency period T of the current time segment, calculating and obtaining the temperature $T_S$ of the seawater in the second sweep frequency period T, namely from the time t=(n+1)T to the time (n+2)T, according to a fiber Bragg grating temperature sensor demodulation algorithm;

step 11: neglecting changes of the refractive index $n_S$ and the temperature $T_S$ of the seawater in each measurement time segment because the refractive index $n_S$ and the temperature $T_S$ of the seawater change relatively slowly, wherein each measurement time segment includes two sweep frequency periods; the reflective indexes $n_S$ of the seawater obtained in the first sweep frequency period T of the time segment, namely from the time t=nT to the time t=(n+1)T, is used as the refractive index $n_S$ of the seawater in the whole time segment, namely from the time t=nT to the time t=(n+2)T; similarly, the temperature $T_S$ of the seawater obtained in the second sweep frequency period T of the time segment, namely from the time t=(n+1)T to the time t=(n+2)T, is used as the temperature $T_S$ of the seawater in the whole time segment, namely from the time t=nT to the time t=(n+2)T;

step 12: solving the following empirical equation according to the obtained reflective index $n_S$ and the temperature $T_S$ of the seawater and the average wavelength $\bar{\lambda}$ $$\left(\bar{\lambda} = \lambda_0 + \frac{\Delta\lambda}{2}\right)$$

output by the sweep frequency laser light source in the current time segment:

$$n_S = n_0 + (n_1 + n_2 T_S + n_3 T_S^2)S + n_4 T_S^2 + \frac{n_5 + n_6 S + n_7 T_S}{\bar{\lambda}} + \frac{n_8}{\bar{\lambda}^2} + \frac{n_9}{\bar{\lambda}^3}$$

calculating the salinity S of the seawater in the current time segment, namely from the time t=nT to the time t=(n+2)T, wherein respective coefficients are as follows:

$n_0=1.31405$, $n_1=1.779\times10^{-4}$, $n_2=-1.05\times10^{-6}$, $n_3=1.6\times10^{-8}$,
$n_4=-2.02\times10^{-6}$, $n_5=15.868$, $n_6=0.01155$, $n_7=-0.00423$,
$n_8=-4382$, $n_9=1.1455\times10^{6}$;

step 13: defining n=n+2, updating the start time of the time segment, pointing at the next time segment; and, step 14: repeating steps 6-13 in a circular way, measuring the salinity S of the seawater in any time segment after the start time t=0, namely from the time t=nT to the time t=(n+2)T, thus implementing real-time detection of the salinity of the seawater, wherein n=0 1 2, . . . .

2. The method for on-line detection of the salinity of the seawater according to claim 1, wherein in step 3, the Bragg wavelength of the reflection spectrum of the temperature detection probe varies along with a temperature change of the seawater; and within a range of the temperature change of the seawater, a variation interval of the Bragg wavelength of the temperature detection probe does not exceed the sweep frequency wavelength range of the sweep frequency laser light source, which means that the Bragg wavelength varies between $\lambda_0$ and $\lambda_0+\Delta\lambda$.

3. The method for on-line detection of the salinity of the seawater according to claim 1, wherein in step 4 the interference light intensity I(t) is:

$$I(t) = \begin{cases} I_S + I_R + 2\sqrt{I_S I_R} \cos\left[\frac{4\pi l(n_S - n_R)}{\lambda_0}\left(1 - \frac{2\Delta\lambda(t-nT)}{T\lambda_0}\right)\right] & nT \leq t \leq nT + \frac{T}{2} \\ I_S + I_R + 2\sqrt{I_S I_R} \cos\left[\frac{4\pi l(n_S - n_R)}{\lambda_0}\left(1 - \frac{2\Delta\lambda(nT-t)}{T\lambda_0}\right)\right] & nT + \frac{T}{2} \leq t \leq (n+1)T \end{cases}$$

wherein, $I_S$ and $I_R$ are respectively a sensing light intensity and a reference light intensity of the interferometer; if the changes of the $I_S$ and $I_R$ in one sweep frequency period T are neglected, $I_S$ and $I_R$ within one sweep frequency period T are regarded as constants, then the interference light intensity I(t) is the sum of a DC component $I_{DC}$ and an AC component $I_{AC}(t)$, namely $$I(t)=I_{DC}+I_{AC}(t),$$

wherein, the DC component $I_{DC}$ of the interference light intensity I(t) is:

$$I_{DC}=I_S+I_R,$$

and the AC component $I_{AC}(t)$ of the interference light intensity I(t) is:

$$I_{AC}(t) = \begin{cases} 2\sqrt{I_S I_R} \cos\left[\frac{4\pi l(n_S - n_R)}{\lambda_0}\left(1 - \frac{2\Delta\lambda(t-nT)}{T\lambda_0}\right)\right] & nT \leq t \leq nT + \frac{T}{2} \\ 2\sqrt{I_S I_R} \cos\left[\frac{4\pi l(n_S - n_R)}{\lambda_0}\left(1 - \frac{2\Delta\lambda(nT-t)}{T\lambda_0}\right)\right] & nT + \frac{T}{2} \leq t \leq (n+1)T \end{cases};$$

in the above equation, $\lambda_0$, $\Delta\lambda$, l, and $n_R$ are constants; the refractive index $n_S$ of the seawater usually changes relatively slowly, so $n_S$ is also regarded as a constant within one sweep frequency period T, and then the AC component $I_{AC}(t)$ is a single-frequency signal, with a frequency $\omega_s$ $$\omega_s = \frac{8\pi(n_S - n_R)l}{\lambda_0}\frac{\Delta\lambda}{\lambda_0 T}.$$

4. The method for on-line detection of the salinity of the seawater according to claim 1, wherein in step 6 the sampling period $T_1$ is required to meet the requirements of a sampling theorem, namely the following condition:

$$T_1 < \frac{2\pi}{2\omega_s} = \frac{\lambda_0^2 T}{8(n_S - n_R)l\Delta\lambda},$$

and the length $L_1$ of the sampling signal sequence I(m) is:

$$L_1 = \frac{T}{T_1}.$$

5. The method for on-line detection of the salinity of the seawater according to claim 1, wherein in step 7 the sampling period $T_2$ is $$T_2 = \frac{T}{1024}.$$

6. The method for on-line detection of the salinity of the seawater according to claim 5, wherein in step 7 the lengths of the sweep frequency synchronous signal sequence V(h) and the temperature reflection light intensity signal sequence G(h) are both $L_2$, and $L_2$ is $$L_2 = \frac{T}{T_2} = 1024.$$

7. The method for on-line detection of the salinity of the seawater according to claim 1, wherein in step 10 the fiber Bragg grating temperature sensor demodulation algorithm comprises the following steps:
  first, finding a maximum temperature reflection light intensity G(h_M) and a corresponding sequence number h_M according to the temperature reflection light intensity signal sequence G(h);
  second, finding a sweep frequency synchronous signal voltage V(h_M) at this moment according to the sequence number h_M corresponding to the maximum temperature reflection light intensity G(h_M);
  third, finding a Bragg wavelength of the fiber grating temperature sensor corresponding to the maximum temperature reflection light intensity G(h_M) according to the sweep frequency synchronous signal voltage V(h_M) corresponding to the sequence number h_M; and,
  fourth, according to the characteristic parameters of the fiber Bragg grating temperature sensor, calculating the current seawater temperature $T_S$ on the basis of the maximum temperature reflection light intensity G(h_M).

8. A device for on-line detection of the salinity of seawater for the method for on-line detection of the salinity of the seawater according to claim 1, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

9. The device for on-line detection of the salinity of the seawater according to claim 8, wherein the water platform comprises a sweep frequency laser light source, a sweep frequency synchronous signal source, a first photoelectric detector, a second photoelectric detector, an A/D converter, a signal processing unit, a control unit, a first 1×2 fiber coupler, a first fiber circulator and a second fiber circulator; the temperature detection probe comprises a fiber Bragg grating temperature sensor; the sweep frequency laser light source is provided with a fiber interface and an electrical interface; the sweep frequency laser light source is connected with the sweep frequency synchronous signal source through the electrical interface; the sweep frequency laser light source is connected with an arm 1 of the first 1×2 fiber coupler through the fiber interface; an arm 2 and an arm 3 of the first 1×2 fiber coupler are respectively connected with an arm 1 of the first fiber circulator and an arm 1 of the second fiber circulator; an arm 2 and an arm 3 of the first fiber circulator are respectively connected with the refractive index detection probe and the first photoelectrical detector; an arm 2 and an arm 3 of the second fiber circulator are respectively connected with the temperature detection probe and the second photoelectric detector; the sweep frequency synchronous signal source, the first photoelectric detector and the second photoelectric detector all are connected with the A/D converter; the A/D converter is connected with the signal processing unit; the signal processing unit is connected with a control unit; and the control unit is also connected with a sweep frequency synchronous signal source.

10. The device for on-line detection of the salinity of the seawater according to claim 8, wherein the refractive index detection probe comprises a second 1×2 fiber coupler, a first fiber self-focusing lens, a second fiber self-focusing lens, a seawater sample cavity, a reference medium, a first reflecting mirror and a second reflecting mirror, wherein an arm 1 of the second 1×2 fiber coupler is connected with the arm 2 of the first fiber circulator; an arm 2 and an arm 3 of the second 1×2 fiber coupler are respectively connected with the first fiber self-focusing lens and the second fiber self-focusing lens; the seawater sample cavity is positioned between the first fiber self-focusing lens and the first reflecting mirror, and the reference medium is positioned between the second fiber self-focusing lens and the second reflecting mirror.

11. A device for on-line detection of the salinity of seawater for the method for on-line detection of the salinity of the seawater according to claim 2, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

12. A device for on-line detection of the salinity of seawater for the method for on-line detection of the salinity of the seawater according to claim 3, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

13. A device for on-line detection of the salinity of seawater for the method for on-line detection of the salinity of the seawater according to claim 4, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

14. A device for on-line detection of the salinity of seawater for the method for on-line detection of the salinity of the seawater according to claim 5, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

15. A device for on-line detection of the salinity of seawater for the method for on-line detection of the salinity of the seawater according to claim 6, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

16. A device for on-line detection of the salinity of seawater for the method for on-line detection of the salinity of the seawater according to claim 7, comprising a water platform, the refractive index detection probe and the temperature detection probe, wherein the water platform is respectively connected with the refractive index detection probe and the temperature detection probe through two fibers; the water platform outputs the frequency modulation light wave of which the wavelength is a periodic saw-tooth wave voltage signal, the frequency modulation light wave is divided into two beams which are respectively transmitted to the refractive index detection probe and the temperature detection probe in seawater; the refractive index detection probe is an interferometer, and the temperature detection probe is internally provided with a fiber Bragg grating.

* * * * *

UNITED STATES PATENT AND TRADEMARK OFFICE
CERTIFICATE OF CORRECTION

PATENT NO. : 10,876,962 B2
APPLICATION NO. : 15/778631
DATED : December 29, 2020
INVENTOR(S) : Bo Zou et al.

Page 1 of 1

It is certified that error appears in the above-identified patent and that said Letters Patent is hereby corrected as shown below:

On the Title Page

Item (30), insert:
-- Foreign Application Priority Data
Jun. 03, 2016 (CN)............201610394000.3 --

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*